United States Patent
Kuzmanich et al.

(10) Patent No.: US 11,078,133 B2
(45) Date of Patent: Aug. 3, 2021

(54) AROMATIC ALKYLATION PROCESS

(71) Applicant: UOP LLC, Des Plaines, IL (US)

(72) Inventors: Gregory B. Kuzmanich, Arlington Heights, IL (US); Richard A. Johnson, II, Algonquin, IL (US); Joseph A. Montalbano, Elmhurst, IL (US); Feng Xu, Winnetka, IL (US); Robert E. Tsai, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/705,791

(22) Filed: Dec. 6, 2019

(65) Prior Publication Data

US 2021/0171421 A1    Jun. 10, 2021

(51) Int. Cl.
| | |
|---|---|
| C07C 2/86 | (2006.01) |
| C07C 2/66 | (2006.01) |
| B01J 8/18 | (2006.01) |

(52) U.S. Cl.
CPC ............. *C07C 2/864* (2013.01); *B01J 8/1809* (2013.01); *B01J 8/1845* (2013.01); *C07C 2/66* (2013.01)

(58) Field of Classification Search
None
See application file for complete search history.

(56) References Cited

U.S. PATENT DOCUMENTS

| | | | |
|---|---|---|---|
| 4,992,607 A * | 2/1991 | Harandi | C07C 2/66 585/322 |
| 5,120,890 A | 6/1992 | Sachtler et al. | |
| 5,599,439 A * | 2/1997 | Collins | C10G 69/08 208/212 |
| 5,939,597 A | 8/1999 | Dessau et al. | |
| 2003/0018231 A1* | 1/2003 | Xu | B01J 29/87 585/640 |
| 2013/0165724 A1 | 6/2013 | Han et al. | |
| 2018/0170842 A1* | 6/2018 | Schmidt | B01J 29/90 |
| 2019/0161420 A1* | 5/2019 | Detjen | C07C 7/04 |

FOREIGN PATENT DOCUMENTS

| | | |
|---|---|---|
| WO | 2018118592 A1 | 6/2018 |
| WO | 2018118595 A1 | 6/2018 |
| WO | 2018118675 A1 | 6/2018 |
| WO | 2018196361 A1 | 11/2018 |

OTHER PUBLICATIONS

Written Opinion from PCT Application No. PCT/US2020/063263 dated Mar. 9, 2021.
International Search Report from PCT/US2020/063263 dated Mar. 9, 2021.

* cited by examiner

*Primary Examiner* — Philip Y Louie
*Assistant Examiner* — Alyssa L Cepluch (57) ABSTRACT

Processes and apparatuses for alkylating aromatic hydrocarbons with an alkylating reagent to produce an alkylated aromatic product are described. The processes and apparatuses use a riser reactor operated at a superficial velocity of 10 m/s to 25 m/s to produce the alkylated aromatic product. In some embodiments, a combination of steam and aromatic hydrocarbon is used to lift the catalyst.

19 Claims, 4 Drawing Sheets

AROMATIC ALKYLATION PROCESS

FIELD

This present disclosure relates to processes and apparatuses for producing an aromatic alkylated product, such as paraxylene, in an aromatics complex. More specifically, the present disclosure relates to processes and apparatuses for aromatic alkylation within an aromatics complex for producing paraxylene. One embodiment uses a riser reactor, another embodiment uses a pre-reactor producing dimethyl ether, and another embodiment provides partial regeneration of the catalyst.

BACKGROUND

The xylene isomers are produced in large volumes from petroleum as feedstocks for a variety of important industrial chemicals. The most important of the xylene isomers is paraxylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of $C_8$ aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated or transalkylated to yield benzene and $C_8$ aromatics from which the individual xylene isomers are recovered.

An aromatics complex flow scheme has been disclosed by Meyers in the HANDBOOK OF PETROLEUM REFINING PROCESSES, 2d. Edition in 1997 by McGraw-Hill, and is incorporated herein by reference.

Traditional aromatics complexes send toluene to a transalkylation zone to generate desirable xylene isomers via transalkylation of the toluene with $A_{9+}$ components. $A_{9+}$ components are present in both the reformate bottoms and the transalkylation effluent. Paraxylene is most often produced from a feedstock which has a methyl to phenyl ratio of less than 2. As a result, the paraxylene production is limited by the available methyl groups in the feed. In addition, paraxylene production also typically produces benzene as a byproduct. Since paraxylene is more valuable than benzene and the other byproducts produced in an aromatics complex, there is a desire to maximize the paraxylene production from a given amount of feed. There are also cases where a paraxylene producer would prefer to avoid the production of benzene as a byproduct of paraxylene production. However, there are also cases where a paraxylene producer would prefer to limit the production of benzene as a byproduct of paraxylene production by making adjustments.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

SUMMARY AND DESCRIPTION

The present subject matter relates to processes and apparatuses for aromatic alkylation in an aromatics complex for producing paraxylene. In some embodiments, the present disclosure relates to processes and apparatuses for toluene methylation in an aromatics complex for producing paraxylene. In some embodiments, the present disclosure relates to processes and apparatuses for aromatic alkylation within an aromatics complex for producing paraxylene wherein an embodiment uses a riser reactor. In some embodiments, the processes and apparatuses use a pre-reactor producing dimethyl ether. In some embodiments, the processes and apparatuses use partial regeneration of the catalyst.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

Definitions

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The following description is not to be taken in a limiting sense, but is made merely for the purpose of describing the general principles of exemplary aspects. The scope of the present disclosure should be determined with reference to the claims.

Toluene is a low value aromatic product that can be selectively alkylated to produce the higher value para-xylene. Para-xylene exists in equilibrium with lower value meta-xylene and ortho-xylene. The thermodynamic equilibrium amount of para-xylene at reaction temperature and pressure is around 24 wt %. Toluene alkylation has the potential to produce higher than equilibrium amounts of para-xylene. High para-xylene selectivity helps to minimize the size of downstream units required to isolate the para-xylene from the less valuable xylene isomers and to convert the less valuable isomers into para-xylene. Reactor design plays an important role in maximizing per pass conversion of toluene while maintaining high selectivity to para-xylene. Most of the existing processes utilize fluidized beds with substantial backmixing to maximize conversion. While conversion can be higher, the lower para-xylene selectivity significantly increases downstream unit sizing and costs. These processes operate with a turbulent fluidized bed having a superficial velocity of less than 3 m/s. For example, U.S. Pat. No. 5,939,597 ('597 patent) describes a toluene methylation process operating at a temperature of about 300-750° C., a pressure of about 101-7000 kPa(g), a WHSV of about 0.5-1000 $hr^{-1}$, a bed density of about 100-600 $kg/m^3$, a molar ratio of toluene to methanol of less than 5, and a superficial velocity of about 0.3-3 m/s. The '597 patent indicates that higher superficial velocities may result in excessive entrainment of fine particles, and that operating above 10 m/s may result in the entire bed being transported out of the reaction zone. WO 2018/196361 describes a turbulent fluidized bed reactor and process for toluene methylation operating at a temperature of about 350-600° C., a pressure of about 97-1000 kPa(g), a bed density of about 200-1200 $kg/m^3$, a molar ratio of toluene to methanol of 0.25-8, and a superficial velocity of about 0.1-2 m/s.

In contrast, the present process discloses a reactor design with high conversion and minimal backmixing that results in higher para-xylene selectivities (e.g., para-xylene/xylene ratio of greater than 0.90, or greater than 0.91, or greater than 0.92, or greater than 0.93, or greater than 0.94) than the prior art (para-xylene/xylene ratio of 0.80-0.85). The riser reactor is operated with a superficial velocity in excess of 10 m/s to minimize backmixing. To achieve these superficial velocities, typical operators use steam to lift the catalyst. However, generating this much steam is very energy intensive and wasteful. A combination of steam and aromatic feeds can be used to minimize the utilities for the aromatic alkylation process, and can reduce utilities by up to 10%, or up to 15%, or up to 20%, or up to 25%, or up to 30%, or at least 10%, or at least 15%, or at least 20%, or at least 25% compared to using 100% steam.

Operating with a superficial velocity in excess of 8 m/s, minimizes the backmixing of the catalyst within the reactor. When superficial velocities are less than 8 m/s, as disclosed in the prior art, catalyst particles can mix non-uniformly within the riser leading to a wide distribution of residence times and non-plug flow gas distributions. This wide variety of residence times leads to under reaction of the aromatic feed at low residence times or back-isomerization of the xylene at higher residence times. In contrast, operation with superficial velocities in excess of 8 m/s has a more ideal plug-flow-like gas distribution. This allows the residence time to be tuned to maximize the aromatic conversion while maintaining high para-xylene selectivities. When the superficially velocity is above 25 m/s, catalyst attrition losses would be prohibitive. The superficial velocity is typically in excess of 8 m/s, or in excess of 9 m/s, or in excess of 10 m/s, or in a range of 8 m/s to 25 m/s, or 9 m/s to 25 m/s, or 10 m/s to 25 m/s.

One aspect of the invention is a process for alkylating an aromatic hydrocarbon with an alkylating reagent to produce an alkylated aromatic product. In one embodiment, the process comprises: passing an aromatic hydrocarbon feed stream and an alkylating reagent feed stream to a riser reactor operated at a superficial velocity of 10 m/s to 25 m/s in the presence of a catalyst to produce a reaction mixture comprising the alkylated aromatic product, light olefins, and unreacted aromatic hydrocarbon; and recovering the alkylated aromatic product.

In some embodiments, the process further comprises introducing one or more of steam or an aromatic hydrocarbon into the riser reactor.

In some embodiments, the riser reactor operates at a temperature of about 300° C. to about 700° C.

In some embodiments, the riser reactor operates at a pressure of about 68 kPa(g) to about 1378 kPa (g).

In some embodiments, the riser reactor has a residence time of about 0.5 seconds to about 6 seconds.

In some embodiments, the riser reactor comprises an operating catalyst density of about 25 $kg/m^3$ to 600 $kg/m^3$.

In some embodiments, the molar ratio of toluene to methanol is less than 4 In some embodiments, the weight hourly space velocity of the riser reactor is about 10 $hr^{-1}$ to about 30 $hr^{-1}$.

In some embodiments, the riser reactor comprises a plurality of injection zones.

In some embodiments, the riser reactor comprises one to four methanol injection points.

In some embodiments, recovering the alkylated aromatic product comprises: separating the reaction mixture in a light olefins column into a light olefins overhead stream comprising the light olefins and a light olefins bottom stream comprising the alkylated aromatic product and the unreacted aromatic hydrocarbon.

In some embodiments, the process further comprises: separating the light olefins bottom stream in an aromatics column into an aromatics overhead stream comprising the unreacted alkylating hydrocarbon and an aromatics bottom stream comprising the alkylated aromatic product.

In some embodiments, the process further comprises: recycling the aromatics overhead stream to the riser reactor.

In some embodiments, the aromatic hydrocarbon feed stream comprises toluene, the alkylating reagent comprises methanol, and the alkylated aromatic product comprises xylene.

In some embodiments, the alkylating reagent comprises methanol, and passing the alkylating reagent feed stream to the riser reactor comprises: passing the alkylating reagent feed stream to a pre-reactor to produce dimethyl ether and water; and passing the dimethyl ether and water to the riser reactor.

In some embodiments, the process further comprises: regenerating the catalyst in a regenerator; and introducing the regenerated catalyst into the riser reactor wherein between 0.5 and 4 wt % coke is present on the regenerated catalyst.

In some embodiments, the process further comprises introducing a stream comprising a combination of steam and the aromatic hydrocarbon into the riser reactor, and wherein a cost of utilities for the riser reactor is reduced by at least 10% compared to introducing a stream comprising 100% steam.

Another aspect of the invention is a process for alkylating an aromatic hydrocarbon with an alkylating reagent comprising methanol to produce an alkylated aromatic product. In one embodiment, the process comprises: passing an aromatic hydrocarbon feed stream comprising toluene and a methanol feed stream to a riser reactor operated at a superficial velocity of 8 m/s to 25 m/s in the presence of a catalyst to produce a reaction mixture comprising the alkylated aromatic product comprising xylene, light olefins, and unreacted toluene; separating the reaction mixture in a light olefins column into a light olefins overhead stream comprising the light olefins and a light olefins bottom stream comprising the alkylated aromatic product and the unreacted toluene; separating the light olefins bottom stream in an aromatics column into an aromatics overhead stream comprising the unreacted toluene and an aromatics bottom stream comprising the aromatics product; and recycling the aromatics overhead stream to the riser reactor.

In some embodiments, the riser reactor conditions comprise one or more of: a temperature of about 300° C. to about 700° C.; a pressure of about 68 kPa(g) to about 1378 kPa (g); a residence time of about 0.5 seconds to about 6 seconds; an operating catalyst density of about 25 kg/m$^3$ to 600 kg/m$^3$; a molar ratio of toluene to methanol is less than 4; or a weight hourly space velocity of about 10 hr$^{-1}$ to about 30 hr$^{-1}$.

In some embodiments, the process further comprises introducing a stream comprising a combination of steam and the aromatic hydrocarbon into the riser reactor, and wherein a cost of utilities for the riser reactor is reduced by at least 10% compared to introducing a stream comprising 100% steam.

The aromatic alkylation process will be described using toluene methylation for ease of discussion. Those of skill in the art will recognize that other aromatic hydrocarbons and alkylating reagents can be used.

Figure 1:
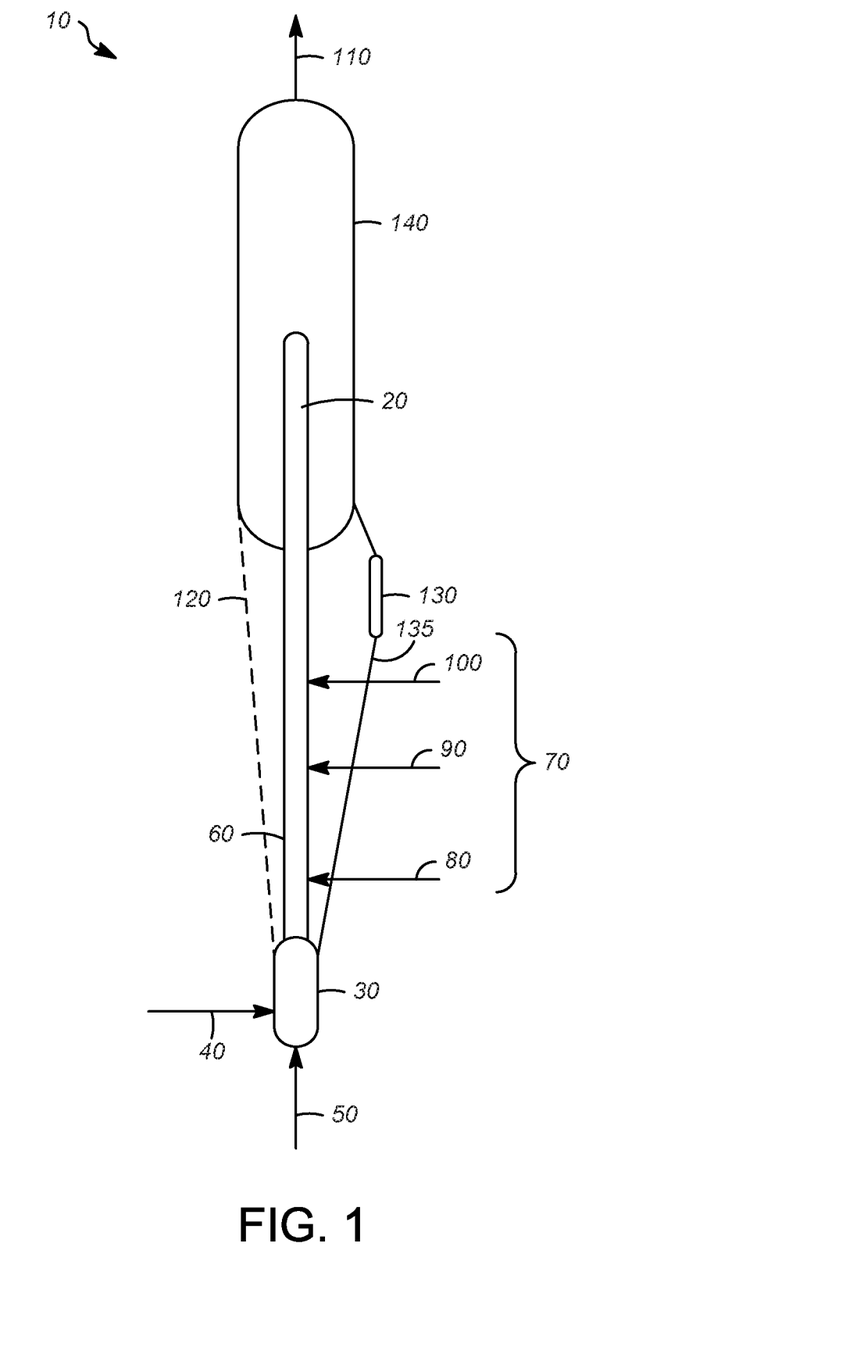
FIG. 1 illustrates a toluene methylation riser reactor having a mixing chamber and a plurality of feed injections.

FIG. 1 illustrates a toluene methylation process 10 having a riser reactor 20 and a mixing chamber 30. FIG. 1 illustrates a process for alkylating an aromatic hydrocarbon reactant with an alkylating reagent to produce an alkylated aromatic product. In some embodiments, the aromatic hydrocarbon feed 40 can be introduced into the mixing chamber 30 comprising water 50. In other embodiments, the aromatic hydrocarbon may be injected directly into the riser reactor 20. In some embodiments, the aromatic hydrocarbons can be introduced in both locations. Additional streams are introduced into the riser reactor 20 which include methanol, toluene, and water. In the example illustrated in FIG. 1, there are a plurality of injection points 70 into the riser portion 60 of the riser reactor 20. In one embodiment, there may be three injection points into the riser reactor 20 above the aromatic hydrocarbon feed 40 and the water 50. The first injection point 80 may comprise a mixture of toluene, methanol, and water. The second injection point 90 and the third injection point 100 may comprise only methanol and water. The aromatic hydrocarbon may include a residence time of about 0.5 seconds to about 6 seconds at a superficial velocity of greater than 8 m/s, for producing the alkylated aromatic product. The alkylate aromatic product stream 110 may include an alkylated aromatic product comprising xylene. Some of the coked catalyst from the reactor 140 may be recirculated to the mixing chamber 30 via line 120.

In some embodiments, the temperature of at least a portion of the coked catalyst can be adjusted as needed. For example, in some embodiments, a fraction of coked catalyst may be cooled in a heater/cooler 130 to remove heat and returned to the mixing chamber via return line 135. In other embodiments, a fraction of coked catalyst may be heated in a heater/cooler 130 to add heat and returned to the mixing chamber via return line 135. Suitable heater/coolers 130 include, but are not limited to, heat exchangers, chillers, electric heaters, fuel fired heaters, and the like.

The riser reactor 20 typically operates at a temperature of about 300° C. to about 700° C., a bed density of about 25 kg/m$^3$ to 600 kg/m$^3$.and a weight hourly space velocity of about 4 hr$^{-1}$ to about 20 hr$^{-1}$. In some embodiments, the weight hourly space velocity of the riser reactor is about 15 hr$^{-1}$. The operating conditions for specific aromatic hydrocarbon alkylation reactions will depend on the particular aromatic hydrocarbon and alkylating reagent. For example, the operating conditions for the alkylation of toluene include at a temperature of about 500° C. to about 700° C., a bed density of about 50 kg/m$^3$ to 325 kg/m$^3$.and a weight hourly space velocity of about 12 hr$^{-1}$ to about 20 hr$^{-1}$.

In an embodiment, the toluene methylation process 10 further includes passing the alkylate aromatic product stream 110 to a light olefins column (not shown) to produce a light olefins overhead stream comprising primarily light olefins and a light olefins bottom stream comprising primarily aromatic compounds comprising the alkylated aromatic product and unreacted aromatic hydrocarbon. By "light olefins," we mean olefins having a carbon number of 5 or lower, primarily those having 2 or 3 carbons. The light olefins bottom stream may be passed to an aromatics column to produce an aromatics overhead stream comprising the unreacted aromatic hydrocarbon and an aromatics column bottom stream comprising the aromatics product stream, such as paraxylene. In some embodiments, the toluene methylation process 10 may include recycling the unreacted aromatic hydrocarbon to the riser reactor.

The catalyst may include a MFI zeolite with silica-to-alumina ratio higher than 20, preferentially higher than 100, a silica or an alumina binder, or combined aluminosilicate binder; and a clay binder. In one embodiment, phosphorus is added to the catalyst. The MFI zeolite content in the catalyst is in the range of about 25 wt % to about 65 wt %. The catalyst may be in a powder format with an average particle size of about 70 microns to about 80 microns.

Figure 2:
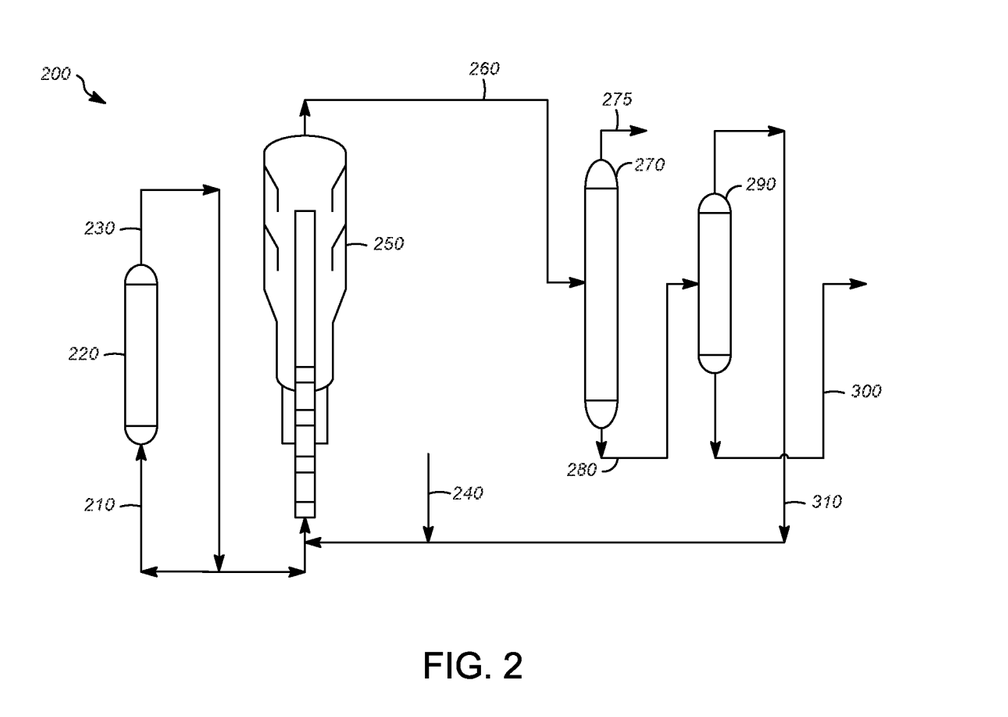
FIG. 2 illustrates a toluene methylation dimethyl ether pre-reactor.

FIG. 2 illustrates a process 200 for alkylating an aromatic hydrocarbon reactant with an alkylating reagent comprising methanol to produce an alkylated aromatic product. The process 200 in FIG. 2 includes passing methanol 210 into a pre-reactor 220 to produce dimethyl ether (DME) and water 230, passing the DME and water 230 and aromatic hydrocarbon such as toluene 240 to a riser reactor 250 for producing the alkylated aromatic product 260. The residence time in the riser reactor 250 may be about 0.5 seconds to about 6 seconds. The aromatic hydrocarbon includes toluene, the alkylating reagent includes methanol or DME, and the alkylated aromatic product 260 includes xylene.

The pre-reactor 220 operates at about 400° C. to about 500° C. The pre-reactor comprises an operating bed density of about 0.30 kg/m$^3$ to about 0.80 kg/m$^3$. In some embodiments, the residence time in the riser reactor is 4 seconds. The weight hourly space velocity of the riser reactor is about 4 to about 20 hr$^{-1}$. The weight hourly space velocity of the riser reactor can be about 10 hr$^{-1}$. The riser reactor system can be operated at a temperature of about 500° C. to about 700° C. The riser reactor system comprises an operating bed density of about 50 kg/m$^3$ to 325 kg/m$^3$.

The pre-reactor may include a plurality of injection zones. The riser reactor may also include a plurality of injection zones, as illustrated in the example in FIG. 1. It is contemplated that the riser reactor comprises about 1 to about 4 injection points. It is also contemplated that the riser reactor may comprise 2 injection points.

In an embodiment, the process 200 further includes passing the alkylated aromatic product 260 to a light olefins column 270 to produce a light olefins overhead stream 275 comprising light olefins and a light olefins bottom stream 280 comprising primarily alkylated aromatic product and unreacted aromatic hydrocarbon. Then the light olefins bottom stream 280 may be passed to an aromatics column 290 to produce an aromatics product stream 300 comprising paraxylene and an aromatics overhead stream 310 comprising unreacted aromatic hydrocarbon. The aromatics overhead stream 310 can be recycled to the riser reactor 250.

The catalyst may include a MFI zeolite with silica-to-alumina ratio higher than 20, preferentially higher than 100; a silica or an alumina binder, or combined aluminosilicate binder; and a clay binder. In one embodiment, phosphorus is added to the catalyst. The MFI zeolite content in the catalyst is in the range of about 25 wt % to about 65 wt %. The catalyst may be in a powder format with an average particle size of about 70 microns to about 80 microns.

Figure 3:
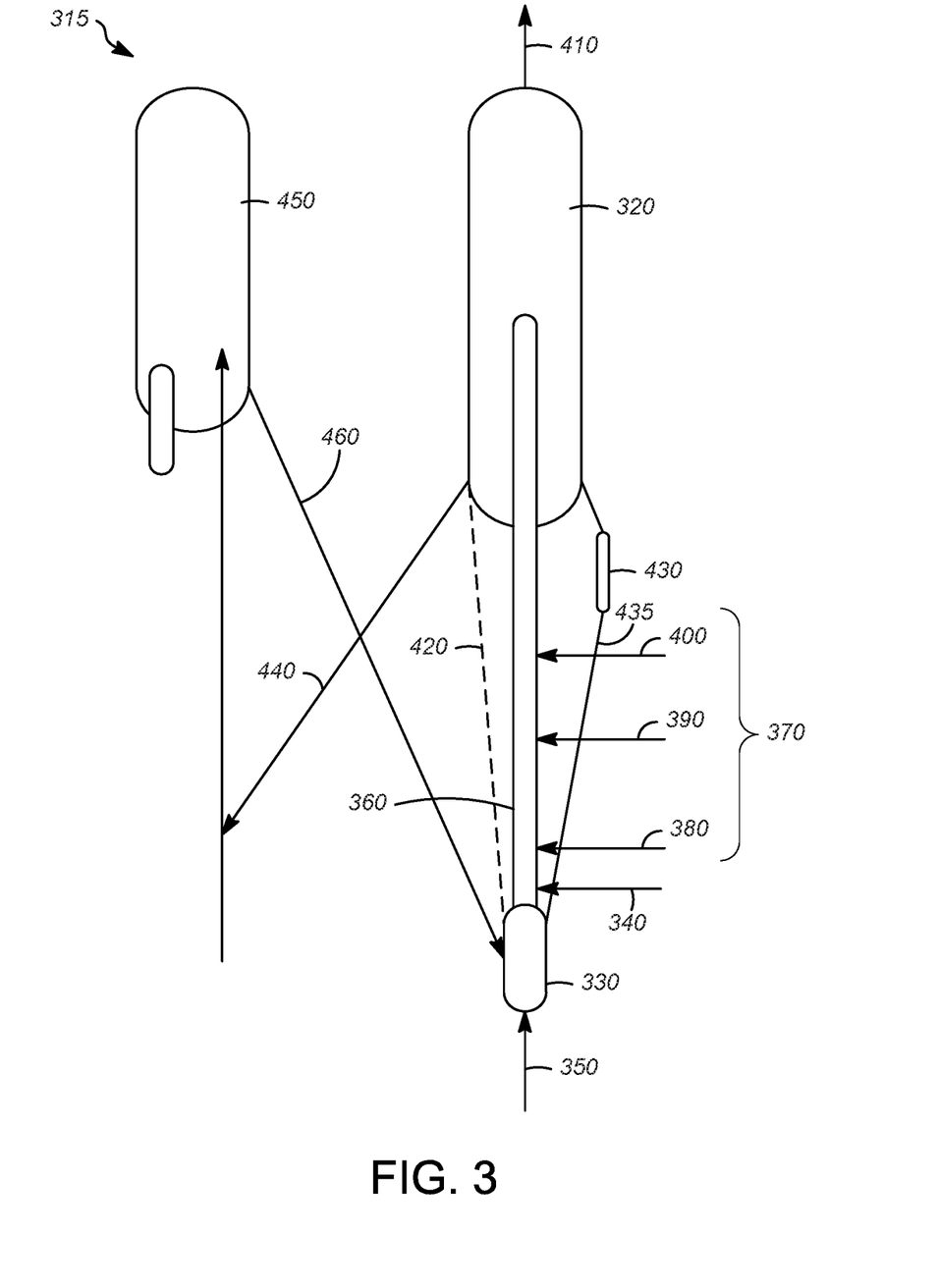
FIG. 3 illustrates a toluene methylation partial regeneration scheme.

FIG. 3 illustrates a toluene methylation process 315 having a riser reactor 320, a mixing chamber 330, and a regenerator 450. More specifically, FIG. 3 illustrates a process for alkylating an aromatic hydrocarbon reactant with an alkylating reagent to produce an alkylated aromatic product. In some embodiments, the aromatic hydrocarbon feed 340 can be introduced above a mixing chamber 330 comprising water 350. In other embodiments, the aromatic hydrocarbon can be injected directly into the riser reactor 320. A portion of the coked catalyst 440 can be sent to the regenerator 450. Additional streams are introduced into the riser reactor 320 which include methanol, toluene, and water. In the example illustrated in FIG. 3, there are a plurality of injection points 370 into the riser portion 360 of the riser reactor 320. In one embodiment there may be three injection points. The first injection point 380 may comprise a mixture of toluene, methanol, and water. The second injection point 390 and the third injection point 400 may comprise only methanol and water. The aromatic hydrocarbon may include a residence time of about 0.5 seconds to about 6 seconds, for producing the alkylated aromatic product. The alkylate aromatic product stream 410 may include an alkylated aromatic product includes xylene. Some of the coked catalyst from the riser reactor 320 may be recirculated to the mixing chamber 330 via line 420. In some embodiments, the temperature of at least a portion of the coked catalyst can be adjusted as needed. For example, in some embodiments, a fraction of coked catalyst may be cooled in a heater/cooler 430 to remove heat and returned to the mixing chamber via return line 435. In other embodiments, a fraction of coked catalyst may be heated in a heater/cooler 430 to add heat and returned to the mixing chamber via return line 435. Suitable heater/coolers 430 include, but are not limited to, heat exchangers, chillers, electric heaters, fuel fired heaters, and the like.

The riser reactor 320 comprises a temperature of about 300° C. to about 700° C. The riser reactor 320 comprises an operating bed density of about 25 kg/m$^3$ to 600 kg/m$^3$. The weight hourly space velocity of the riser reactor 320 is about 4 hr$^{-1}$ to about 20 hr$^{-1}$. The weight hourly space velocity of the riser reactor is about 15 hr$^{-1}$.

In an embodiment, the regenerator 450 produces a product stream of catalyst 460 wherein about 0.1% to about 15% of coke is left on the catalyst and the partially regenerated catalyst 460 is returned to the riser reactor 320. In a preferred embodiment, the regenerator 450 produces a product stream of catalyst 460 wherein about 2% to about 4% of coke is left on the catalyst, and the partially regenerated catalyst 460 is returned to the riser reactor 320. Suitable regenerators include, but are not limited to, bubbling bed regenerators, swing bed regenerators, fixed bed regenerators, and combustor regenerators, including fast fluidized combustor regenerators. The oxygen concentration at the inlet may be about 0.5% to about 100%, or about 0.5% to about 21.0%.

In an embodiment, the toluene methylation process 315 further includes passing the alkylate aromatic product stream 410 to a light olefins column (not shown) to produce a light olefins overhead stream comprising light olefins and a light olefins bottom stream comprising primarily aromatic compounds comprising the alkylated aromatic product and unreacted aromatic hydrocarbon. The light olefins bottom stream may be passed to an aromatics column to produce an aromatics overhead stream comprising the unreacted aromatic hydrocarbon, such as toluene, and an aromatics bottom stream comprising the aromatics product stream, such as paraxylene. In some embodiments, the toluene methylation process 315 may include recycling the unreacted aromatic hydrocarbon to the riser reactor.

The catalyst may include a MFI zeolite with silica-to-alumina ratio higher than 20, preferentially higher than 100; a silica or an alumina binder, or combined aluminosilicate binder; and a clay. In one embodiment, phosphorus is added to the catalyst. The MFI zeolite content in the catalyst is in the range of about 25 wt % to about 65 wt %. The catalyst may be in a powder format with an average particle size of about 70 microns to about 80 microns.

EXAMPLES

The following examples are intended to further illustrate the subject embodiments.

These illustrations of different embodiments are not meant to limit the claims to the particular details of these examples.

Figure 4:
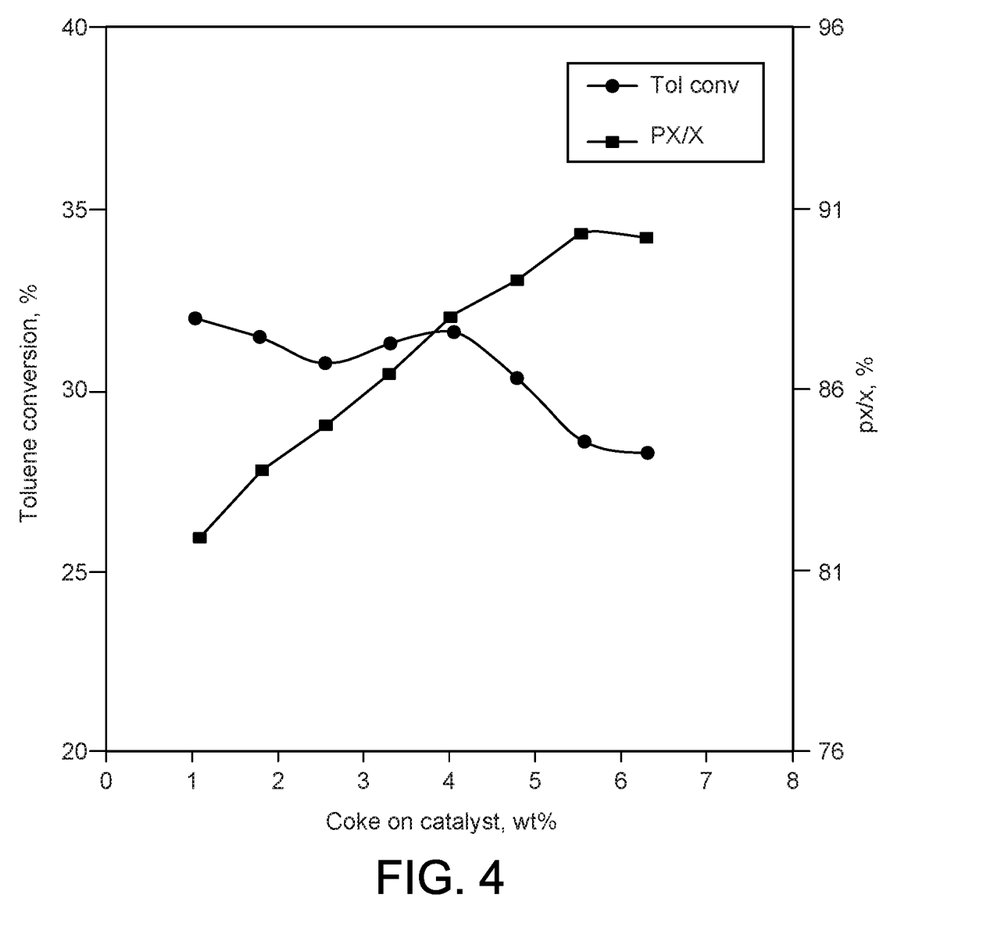
FIG. 4 illustrates the performance of a partially regenerated spent catalyst of up to 6 wt % coke on catalyst is sent back to the riser.

FIG. 4 illustrates that partial regeneration of a spent catalyst to retain up to 6 wt % coke on catalyst back to the riser would improve 3-5% PX/X selectivity. Additional residual coke levels above 2% and up to 6% allows PX/X to continue to increase without a significant and adverse effect on catalyst activity allowing PX/X to be maximized will still maintaining an acceptable toluene conversion. The catalyst comprises 40 wt % MFI zeolite with silica-to-alumina ratio of 500 and was steamed under 1050° C. for 45 minutes.

SPECIFIC EMBODIMENTS

While the following is described in conjunction with specific embodiments, it will be understood that this description is intended to illustrate and not limit the scope of the preceding description and the appended claims.

A first embodiment of the invention is a process for alkylating an aromatic hydrocarbon with an alkylating reagent to produce an alkylated aromatic product, comprising passing an aromatic hydrocarbon feed stream and an alkylating reagent feed stream to a riser reactor operated at a superficial velocity of 10 m/s to 25 m/s in the presence of a catalyst to produce a reaction mixture comprising the alkylated aromatic product, light olefins, and unreacted aromatic hydrocarbon; and recovering the alkylated aromatic product. An embodiment of the invention is one, any or all of prior embodiments in this paragraph up through the first embodiment in this paragraph further comprising introducing one or more of steam or an aromatic hydrocarbon into the riser reactor. An embodiment of the invention is one, any or all of prior embodiments in this paragraph up through the first embodiment in this paragraph, wherein the riser reactor operates at a temperature of about 300° C. to about 700° C. An embodiment of the invention is one, any or all of prior embodiments in this paragraph up through the first embodiment in this paragraph, wherein the riser reactor operates at a pressure of about 68 kPa(g) to about 1378 kPa (g). An embodiment of the invention is one, any or all of prior embodiments in this paragraph up through the first embodiment in this paragraph wherein the riser reactor has a residence time of about 0.5 seconds to about 6 seconds. An embodiment of the invention is one, any or all of prior embodiments in this paragraph up through the first embodiment in this paragraph, wherein the riser reactor comprises an operating catalyst density of about 25 kg/m$^3$ to 600 kg/m$^3$. An embodiment of the invention is one, any or all of prior embodiments in this paragraph up through the first embodiment in this paragraph wherein a molar ratio of toluene to methanol is less than 4. An embodiment of the invention is one, any or all of prior embodiments in this paragraph up through the first embodiment in this paragraph, wherein a weight hourly space velocity of the riser reactor is about 10 hr$^{-1}$ to about 30 hr$^{-1}$. An embodiment of the invention is one, any or all of prior embodiments in this paragraph up through the first embodiment in this paragraph, wherein the riser reactor comprises a plurality of injection zones. An embodiment of the invention is one, any or all of prior embodiments in this paragraph up through the first embodiment in this paragraph, wherein the riser reactor comprises one to four methanol injection points. An embodiment of the invention is one, any or all of prior embodiments in this paragraph up through the first embodiment in this paragraph, wherein recovering the alkylated aromatic product comprises separating the reaction mixture in a light olefins column into a light olefins overhead stream comprising the light olefins and a light olefins bottom stream comprising the alkylated aromatic product and the unreacted aromatic hydrocarbon. An embodiment of the invention is one, any or all of prior embodiments in this paragraph up through the first embodiment in this paragraph, further comprising separating the light olefins bottom stream in an aromatics column into an aromatics overhead stream comprising the unreacted alkylating hydrocarbon and an aromatics bottom stream comprising the alkylated aromatic product. An embodiment of the invention is one, any or all of prior embodiments in this paragraph up through the first embodiment in this paragraph, further comprising recycling the aromatics overhead stream to the riser reactor. An embodiment of the invention is one, any or all of prior embodiments in this paragraph up through the first embodiment in this paragraph, wherein the aromatic hydrocarbon feed stream comprises toluene, the alkylating reagent comprises methanol, and the alkylated aromatic product comprises xylene. An embodiment of the invention is one, any or all of prior embodiments in this paragraph up through the first embodiment in this paragraph wherein the alkylating reagent comprises methanol, and wherein passing the alkylating reagent feed stream to the riser reactor comprises passing the alkylating reagent feed stream to a pre-reactor to produce dimethyl ether and water; and passing the dimethyl ether and water to the riser reactor. An embodiment of the invention is one, any or all of prior embodiments in this paragraph up through the first embodiment in this paragraph further comprising regenerating the catalyst in a regenerator; and introducing the regenerated catalyst into the riser reactor wherein between 0.5 and 4 wt % coke is present on the regenerated catalyst. An embodiment of the invention is one, any or all of prior embodiments in this paragraph up through the first embodiment in this paragraph further comprising introducing a stream comprising a combination of steam and the aromatic hydrocarbon into the riser reactor, and wherein a cost of utilities for the riser reactor is reduced by at least 10% compared to introducing a stream comprising 100% steam.

A second embodiment of the invention is a process for alkylating an aromatic hydrocarbon with an alkylating reagent comprising methanol to produce an alkylated aromatic product, comprising passing an aromatic hydrocarbon feed stream comprising toluene and a methanol feed stream to a riser reactor operated at a superficial velocity of 8 m/s to 25 m/s in the presence of a catalyst to produce a reaction mixture comprising the alkylated aromatic product comprising xylene, light olefins, and unreacted toluene; separating the reaction mixture in a light olefins column into a light olefins overhead stream comprising the light olefins and a light olefins bottom stream comprising the alkylated aromatic product and the unreacted toluene; separating the light olefins bottom stream in an aromatics column into an aromatics overhead stream comprising the unreacted toluene and an aromatics bottom stream comprising the aromatics product; and recycling the aromatics overhead stream to the riser reactor. An embodiment of the invention is one, any or all of prior embodiments in this paragraph up through the second embodiment in this paragraph wherein riser reactor conditions comprise one or more of a temperature of about 300° C. to about 700° C.; a pressure of about 68 kPa(g) to about 1378 kPa (g); a residence time of about 0.5 seconds to about 6 seconds; an operating catalyst density of about 25 kg/m$^3$ to 600 kg/m$^3$; a molar ratio of toluene to methanol is less than 4; or a weight hourly space velocity of about 10 hr$^{-1}$ to about 30 hr$^{-1}$. An embodiment of the invention is one, any or all of prior embodiments in this paragraph up through the second embodiment in this paragraph further comprising introducing a stream comprising a combination of steam and the aromatic hydrocarbon into the riser reactor, and wherein a cost of utilities for the riser reactor is reduced by at least 10% compared to introducing a stream comprising 100% steam.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for alkylating an aromatic hydrocarbon with an alkylating reagent to produce an alkylated aromatic product, comprising:
   passing an aromatic hydrocarbon feed stream comprising an aromatic hydrocarbon and an alkylating reagent feed stream comprising an alkylating reagent to a riser reactor operated at a superficial velocity of 10 m/s to 25 m/s in the presence of a catalyst to produce a reaction mixture comprising the alkylated aromatic product, light olefins, and unreacted aromatic hydrocarbon, wherein the riser reactor comprises an operating catalyst density of about 325 kg/m$^3$ to 600 kg/m$^3$; and
   recovering the alkylated aromatic product.

2. The process of claim 1 further comprising introducing one or more of steam or additional aromatic hydrocarbon into the riser reactor at a location in the riser reactor above where the aromatic hydrocarbon feed stream and the alkylating reagent feed stream are introduced.

3. The process of claim 1, wherein the riser reactor operates at a temperature of about 300° C. to about 700° C.

4. The process of claim 1, wherein the riser reactor operates at a pressure of about 68 kPa(g) to about 1378 kPa (g).

5. The process of claim 1 wherein the riser reactor has a residence time of about 0.5 seconds to about 6 seconds.

6. The process of claim 2 wherein the aromatic hydrocarbon comprises toluene and the alkylating reagent comprises methanol, and wherein a molar ratio of toluene to methanol is less than 4.

7. The process of claim 1, wherein a weight hourly space velocity of the riser reactor is about 10 hr$^{-1}$ to about 30 hr$^{-1}$.

8. The process of claim 1, wherein the riser reactor comprises a plurality of injection zones.

9. The process of claim 1, wherein the riser reactor comprises one to four alkylating reagent injection points.

10. The process of claim 1, wherein recovering the alkylated aromatic product comprises:
    separating the reaction mixture in a light olefins column into a light olefins overhead stream comprising the light olefins and a light olefins bottom stream comprising the alkylated aromatic product and the unreacted aromatic hydrocarbon.

11. The process of claim 10, further comprising:
    separating the light olefins bottom stream in an aromatics column into an aromatics overhead stream comprising the unreacted aromatic hydrocarbon and an aromatics bottom stream comprising the alkylated aromatic product.

12. The process of claim 11, further comprising:
    recycling the aromatics overhead stream to the riser reactor.

13. The process of claim 1, wherein the aromatic hydrocarbon feed stream comprises toluene, the alkylating reagent comprises methanol, and the alkylated aromatic product comprises xylene, and wherein a para-xylene/xylene ratio of the alkylated aromatic product is greater than 0.90.

14. The process of claim 1 wherein the alkylating reagent comprises methanol, and wherein passing the alkylating reagent feed stream to the riser reactor comprises:
    passing the alkylating reagent feed stream to a pre-reactor to produce dimethyl ether and water; and
    passing the dimethyl ether and water to the riser reactor.

15. The process of claim 1 further comprising:
    regenerating the catalyst in a regenerator; and
    introducing the regenerated catalyst into the riser reactor wherein between 0.5 and 4 wt % coke is present on the regenerated catalyst.

16. The process of claim 1 further comprising introducing a stream comprising a combination of steam and the aromatic hydrocarbon into the riser reactor, and wherein a cost of utilities for the riser reactor is reduced by at least 10% compared to introducing a stream comprising 100% steam.

17. A process for alkylating an aromatic hydrocarbon with an alkylating reagent comprising methanol to produce an alkylated aromatic product, comprising:
    passing an aromatic hydrocarbon feed stream comprising toluene and a methanol feed stream to a riser reactor operated at a superficial velocity of 8 m/s to 25 m/s in the presence of a catalyst to produce a reaction mixture comprising the alkylated aromatic product comprising xylene, light olefins, and unreacted toluene, wherein an operating catalyst density is about 325 kg/m$^3$ to 600 kg/m$^3$ and a para-xylene/xylene ratio of the alkylated aromatic product is greater than 0.90;
    separating the reaction mixture in a light olefins column into a light olefins overhead stream comprising the light olefins and a light olefins bottom stream comprising the alkylated aromatic product and the unreacted toluene;
    separating the light olefins bottom stream in an aromatics column into an aromatics overhead stream comprising the unreacted toluene and an aromatics bottom stream comprising the aromatics product; and
    recycling the aromatics overhead stream to the riser reactor.

18. The process of claim 17 wherein riser reactor conditions comprise one or more of: a temperature of about 300° C. to about 700° C.; a pressure of about 68 kPa(g) to about 1378 kPa (g); a residence time of about 0.5 seconds to about 6 seconds; an operating catalyst density of about 25 kg/m$^3$ to 600 kg/m$^3$; a molar ratio of toluene to methanol is less than 4; or a weight hourly space velocity of about 10 hr$^{-1}$ to about 30 hr$^{-1}$.

19. The process of claim 17 further comprising introducing a stream comprising a combination of steam and the aromatic hydrocarbon into the riser reactor, and wherein a cost of utilities for the riser reactor is reduced by at least 10% compared to introducing a stream comprising 100% steam.

* * * * *